United States Patent [19]

Fauland et al.

[11] 4,436,742
[45] Mar. 13, 1984

[54] 4-HYDROXY-2,1,3-BENZTHIADIAZOLE COMPOUNDS AND β-ADRENERGIC METHOD OF USE THEREFOR

[75] Inventors: Erich Fauland, Mannheim-Gartenstadt; Wolfgang Kampe, Heddesheim; Kurt Stach, Mannheim-Waldhof; Wolfgang Bartsch, Viernheim, all of Fed. Rep. of Germany

[73] Assignee: Boehringer Mannheim GmbH, Mannheim, Fed. Rep. of Germany

[21] Appl. No.: 208,741

[22] Filed: Nov. 20, 1980

Related U.S. Application Data

[63] Continuation of Ser. No. 535,902, Dec. 23, 1974, abandoned.

[30] Foreign Application Priority Data

Feb. 1, 1974 [DE] Fed. Rep. of Germany ....... 2404858

[51] Int. Cl.³ .................. D61K 31/41; C07D 285/06
[52] U.S. Cl. .................................. 424/269; 424/270; 548/127
[58] Field of Search ........................ 548/127; 424/269

[56] References Cited

U.S. PATENT DOCUMENTS 3,655,661  4/1972  Wasson ............................... 548/127

Primary Examiner—Paul M. Coughlan, Jr.
Assistant Examiner—David B. Springer
Attorney, Agent, or Firm—Felfe & Lynch

[57] ABSTRACT

New amine derivatives of 4-hydroxy-2,1,3-benzthiadiazoles of the formula:

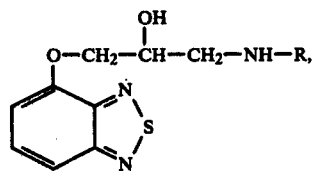

wherein
R is straight-chained or branched alkyl and the pharmacologically compatible salts thereof, that are markedly effected as inhibitors of adrenogenic β-receptors and thus useful for the treatment and prophylaxis of cardiac and circulatory diseases.

10 Claims, No Drawings

4-HYDROXY-2,1,3-BENZTHIADIAZOLE COMPOUNDS AND β-ADRENERGIC METHOD OF USE THEREFOR

This is a continuation of application Ser. No. 535,902, filed Dec. 23, 1974, now abandoned.

The present invention relates to novel 4-hydroxy-2,1,3-benzthiadiazole amine compounds, and to therapeutic compositions and uses thereof.

The new amine derivatives of 4-hydroxy-2,1,3-benzthiadiazole according to the present invention are compounds of the general formula

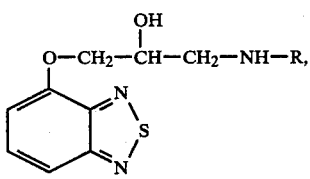

wherein R is straight-chained or branched alkyl and the pharmacologically compatible salts thereof.

The alkyl radicals R in the above-given general formula (I) are preferably branched and can contain up to 6 carbon atoms and preferably contain 3 or 4 carbon atoms.

The new compounds according to the present invention and the pharmacologically compatible salts thereof bring about an inhibition of adrenogenic β-receptors and are, therefore, useful for the treatment and prophylaxis of cardiac and circulatory diseases.

German Patent Specification No. 1,925,989 describes 5-[3-(substituted-amino)-2-hydroxy-propoxy]-2,1,3-benzthiadiazoles which exhibit β-adrenogenic blocking properties. Surprisingly, the new compounds according to the present invention are just as strongly effective as the previously described compounds but in substantially lower dosages. A comparison of the effective dosage with the toxic dosage gives a much more favorable ratio for the new compounds according to the present invention. Those compounds of general formula (I) are especially effective in which R is a branched alkyl radical, preferably a tert.-butyl or isopropyl radical.

The new compounds of formula (I) according to the present invention can be prepared, for example, by one of the following methods:

(a) reaction of a compound of the formula:

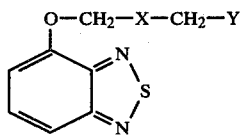

with a compound of the formula:

Z-R      (III), in which R has the same meaning as above, one of the symbols Y and Z stands for an amino group and the other for a reactive group and X is a =C=O group or a =CH-A group, in which A is a hydroxyl group or, together with Y, represents an oxygen atom, and, when X is a =C=O group, the product obtained is subsequently reduced; or (b) reaction of a compound of the formula:

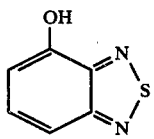

with a compound of the formula:

Y-CH₂-X-CH₂-NH-R      (V), in which R, X and Y have the same meaning as above, and, when X is a =C=O group, the product obtained is subsequently reduced, whereafter, if desired, the product obtained is converted into a pharmacologically compatible salt.

The reactive groups Y and Z in the compounds of formulae (II), (III) and (V) are, in particular, acid residues, for example, of hydrohalic or sulfonic acids.

The reaction of the compounds of formula (II) with compounds of formula (III) according to method (a), as well as of compounds of formula (IV) with compounds of formula (V) according to method (b), is preferably carried out in an organic solvent which is inert under the reaction conditions employed, for example, ethanol, n-butanol, dioxan or dimethyl formamide. The reaction can also be carried out by mixing molar amounts of the reaction components and leaving the mixture to stand at ambient temperature or by heating.

The reaction of the compounds of formula (IV) with the compounds of formula (V) according to method (b) is preferably carried out with the exclusion of oxygen in the presence of an acid acceptor. However, an alkali metal salt of the hydroxy compound of formula (IV) can also be used.

When it is necessary to carry out the reduction of a =C=O group, this can be carried out by catalytic hydrogenation or by means of other appropriate reducing agents, for example, complex metal hydrides, such as sodium borohydride. Preferably, however, catalytic hydrogenation is employed using known catalysts, for example, noble metal catalysts or nickel catalysts in conventional solvents, for example, an alcohol or dioxan.

The present invention is also concerned with 1-[2,1,3-benzthiadiazol-4-yloxy]-2,3-epoxypropane, which is preferably used as starting material, as well as with those embodiments of the process according to the present invention in which there is used a starting material in the form of a crude mixture formed under the reaction conditions or in the form of a salt.

The new compounds of formula (I) can be converted into their pharmacologically compatible salts by reaction, in an organic solvent, with an equivalent amount of an inorganic or organic acid, for example, hydrochloric acid, hydrobromic acid, phosphoric acid, sulfuric acid, acetic acid, citric acid or maleic acid.

The following examples are given for the purpose of illustrating, without limiting, the present invention:

EXAMPLE 1

Preparation of 4-(3-isopropylamino-2-hydroxypropyloxy)-2,1,3-benzthiadiazole 5.2 g (25 mM) 4-(2,3-epoxypropyloxy)-2,1,3-benzthiadiazole in 60 ml. dioxan were heated under reflux for 4 hours with 30 ml. isopropylamine. The reaction mixture was then evaporated and the residue was chromatographed on a silica gel column (silica gel particle size 0.063–0.200 mm., elution agent methanol with a small addition of glacial acetic acid). The residue obtained after evaporation of the eluted fractions was recrystallized from diisopropyl ether. There were obtained 4.1 g (62% of theory) 4-(3-isopropylamino-2-hydroxy-propyloxy)-2,1,3-benzthiadiazole, which had a melting point of 100°–102° C.

The 4-(2,3-epoxypropyloxy)-2,1,3-benzthiadiazole used as starting material was prepared in the following manner:

7.6 g (50 mM) 4-hydroxy-2,1,3-benzthiadiazole were dissolved in 100 ml. dioxan and mixed with 50 ml. epichlorohydrin and 55 ml. 1 N aqueous sodium hydroxide solution and the reaction mixture stirred for 4–5 hours at 55°–60° C. When the reaction was finished, the reaction mixture was diluted with 300 ml. water and extracted with chloroform. The dried chloroform solution was evaporated and the residue was chromatographed on a silica gel column (elution agent: chloroform). The residue obtained after evaporation of the elution fractions crystallized upon treatment with diisopropyl ether. There were obtained 7.2 g (69% of theory) 4-(2,3-epoxypropyloxy)-2,1,3-benzthiadiazole, which had a melting point of 65°–67° C.

EXAMPLE 2

Preparation of 4-(3-tert.-butylamino-2-hydroxypropyloxy)-2,1,3-benzthiadiazole 12.5 g (60 mM) 4-(2,3-epoxypropyloxy)-2,1,3-benzthiadiazole were dissolved in 150 ml. n-butanol and, after the addition of 40 ml. tert.-butylamine, heated under reflux for 3 hours. When the reaction was finished, the reaction mixture was evaporated and the residue was chromatographed on a silica gel column in the manner described in Example 1. There were obtained 9.6 g (57% of theory) 4-(3-tert.-butylamino-2-hydroxy-propyloxy)-2,1,3-benzthiadiazole, which had a melting point of 89°–91° C.

As noted above, the compounds of the instant invention have cardiac β-receptor blocking activity, and are therefore useful for the treatment and prophylaxis of cardiac and circulatory diseases e.g., cardiac hypoxia.

The following tests were carried out to determine the cardiac β-receptor blocking activity of certain test compounds by determining the inhibition of the heart beat frequency increase induced by intravenous administration of isoprenalin.

The test compounds representative of the invention were the following:

Compound I 4-(3-Isopropylamino-2-hydroxy-propyloxy)-2,1,3-benzthiadiazole

Compound II 4-(3-Tert.-Butylamino-2-hydroxy-propyloxy-2,1,3-benzthiadiazole

As a comparison compound there was included:

Compound A 5-(3-Isopropylamino-2-hydroxypropoxy)-2,1,3-benzothiadiazole

These compounds were tested in the following manner:

1. The acute toxicity in mice when administered intravenouly was measured and the $LD_{50}$ (=dosage at which 50% of the mice die) determined. The results were set forth in the table below.

The β-receptor blocking activity of the test compounds was tested on wake rabbits weighing between 2 to 3.5 kg. and kept in wooden cages. EKG-electrodes were inserted into the hind quarters of the rabbits s.c. (II. lead) and the heart frequency was measured based on 20 heart beats. The test compounds were then infused through a small tube to the ear vein of the rabbits over a period of 15 minutes. 30 minutes after the infusion isoprenalin (3,4-dihydro-α-[(isopropylamino)-methyl]-benzylalcohol) was injected intravenously at 1 μg/kg.

The results are set forth in terms of inhibition of isoprenalin tachycardia, and are set forth in the table below:

TABLE

| Test Substance | Acute Toxicity $LD_{50}$ Mouse mg/kg i.v. | Blocking of Isoprenalin Tachycardia in wake rabbits | | $DE_{250}$* mg/kg i.v. |
|---|---|---|---|---|
| | | Dosage mg/kg i.v. | Heartbeat Frequency $\bar{x} \pm sx$ | |
| Control | — | without Isoprenalin | 205 ± 9 | — |
| Control | — | with Isoprenalin | 338 ± 10 | — |
| Comparison | | | | |
| Compound A | 100 | 1 | 290 ± 8 | 5 |
| | | 5 | 246 ± 7 | |
| Compound I | 50 | 0.01 | 324 ± 9 | 0.7 |
| | | 0.1 | 297 ± 10 | |
| | | 0.3 | 266 ± 14 | |
| | | 1.0 | 220 ± 14 | |
| | | 5.0 | 210 ± 5 | |
| Compound II | 45 | 0.1 | 308 ± 10 | 0.5 |
| | | 0.5 | 245 ± 6 | |
| | | 1.0 | 215 ± 10 | |
| | | 5.0 | 220 ± 7 | |

*Interpolated dosage which limits the frequence increase to 250 beats/min.

The above data show that the test compounds representative of the invention block tachycardia, depending on the administered dosage. The inventive compounds are already effective at dosages about 7 to 10 times smaller than the dosages required of the comparison compound in order to give the same tachycardia blocking effect.

Also, it will be seen that the inventive compounds provide a far greater margin of safety in that the margin between the dosage which is toxic to mice, and the dosage giving tachycardia blocking, is very large and substantially larger than the margin provided by the comparison compound. Thus, the dosage at which the test compounds limited the heartbeat frequency increase induced by isoprenalin to 250 beats per minute (as determined by interpolation and set forth in the table as $DE_{250}$) to the $LD_{50}$ dosage was as follows for the respective compounds:

Compound A 5-(3-Isopropylamino-2-hydroxypropoxy)-2,1,3-benzthiadiazole: 1:20

Compound I 4-(3-Isopropylamino-2-hydroxy-propyloxy)-2,1,3-benzthiadiazole: 1:70

Compound II 4-(3-Tert.-Butylamino-2-hydroxy-propyloxy-2,1,3-benzthiadiazole: 1:90

Accordingly, the therapeutic safety of the inventive compounds is 3.5 to 4.5 times that of the comparison compound.

The compounds according to the present invention are thus unexpectedly superior in effectiveness to known compounds and thus present a valuable contribution to the art.

The dosage of the novel compounds of the present invention depends on the age, weight, and condition of the patient being treated. Generally speaking, for aduloral administration, the preferred unit dosage of active compound with a suitable pharmaceutical diluent or lubricant is 1 mg.–40 mg. four times a day. In general the oral dosage is 20–40 mg., whereas the intravenous dosage is generally 1–5 mg., four times a day.

For the preparation of pharmaceutical compositions, at least one of the new compounds according to the present invention is mixed with appropriate solid or liquid pharmaceutical diluents or carriers and, if desired, also with odoriferous, flavoring and coloring material and then formed into, for example, tablets or dragees or, with the addition of appropriate adjuvants, suspended or dissolved in water or oil, for example in olive oil.

The new compounds according to the present invention of general formula (I) and the salts thereof can be administered enterally or parentally in solid or liquid form. As injection medium, it is preferred to use water which contains the conventional additives for injection solutions, for example, stabilizing agents, solubilizing agents or buffers. Additives of this kind include, for example, tartrate and citrate buffers, ethanol, complex-forming agents (such as ethylenediamine-tetraacetic acid and the non-toxic salts thereof), and high molecular weight polymers (such as polyethylene oxide) for viscosity regulation. Solid carrier materials include, for example, starch, lactose, mannitol, methyl cellulose, talc, highly-dispersed silicic acids, high molecular weight fatty acids (such as stearic acid), gelatine, agaragar, calcium phosphate, magnesium stearate, animal and vegetable fats and solid high molecular weight polymers (such as polyethylene glycols); compositions which are suitable for oral administration can, if desired, contain flavoring and sweetening agents.

For preparing compounds such as tablets and other compressed formulations, the compounds can include any compatible and edible tableting material used in pharmaceutical practice as for example, corn starch, lactose, stearic acid, magnesium stearate, talc, methyl cellulose and the like.

Similarly the compounds of the present invention can be mixed with suitable adjuvants for the preparation of resorbable hard gelatin or soft capsules utilizing conventional pharmaceutical practices.

Further, the compounds can be employed in the form of their solutions or suspensions suitable for parenteral administration.

It will be appreciated that the instant specification and examples are set forth by way of illustration and not limitation, and that various modifications and changes may be made without departing from the spirit and scope of the present invention.

What is claimed is:

1. 4-Hydroxy-2,1,3-benzthiadiazole amine compound of the formula:

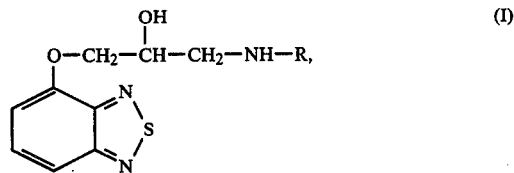

wherein

R is branched alkyl of 3 or 4 carbon atoms and the pharmacologically compatible salts thereof.

2. 4-Hydroxy-2,1,3-benzthiadiazole amine compound as claimed in claim 1, wherein R is a branched alkyl of 3 carbon atoms.

3. Compound as claimed in claim 2, wherein R is a branched alkyl radical containing from 3 to 4 carbon atoms.

4. Compound as claimed in claim 1, designated 4-(3-isopropylamino-2-hydroxy-propyloxy)-2,1,3-benzthiadiazole.

5. Compound as claimed in claim 1, designated 4-(3-tert.-butylamino-2-hydroxy-propyloxy)-2,1,3-benzthiadiazole.

6. Therapeutic composition for treating cardiac or circulatory insufficiencies in mammals susceptible to treatment by beta-adrenergic agents comprising a therapeutically effective amount of a 4-hydroxy-2,1,3-benzthiadiazole amine compound as claimed in claim 1 in admixture with a pharmaceutically acceptable carrier therefor.

7. Method for treating cardiac or circulatory insufficiencies in mammals susceptible to treatments by beta-adrenergic agents which comprises the step of administering to the mammal a 4-hydroxy-2,1,3-benzthiadiazole amine compound of the formula

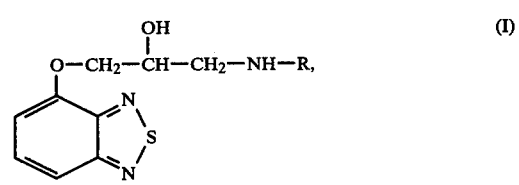

wherein

R is branched alkyl of 3 or 4 carbon atoms, or a pharmacologically compatible salt thereof, in a therapeutically effective amount.

8. Method as claimed in claim 7, wherein the said insufficiency is cardiac hypoxia.

9. Method as claimed in claim 7, wherein said compound is administered of a dosage of from 1 to 40 mg.

10. Method as claimed in claim 7, wherein said compound is at least one of the following:

4-(3-isopropylamino-2-hydroxy-propyloxy)-2,1,3-benzthiadiazole.

4-(3-tert.-butylamino-2-hydroxy-propyloxy)-2,1,3-benzthiadiazole.

* * * * *

UNITED STATES PATENT AND TRADEMARK OFFICE
CERTIFICATE OF CORRECTION

PATENT NO. : 4,436,742

DATED : March 13, 1984

INVENTOR(S) : Erich Fauland et al.

It is certified that error appears in the above-identified patent and that said Letters Patent is hereby corrected as shown below:

Title page, Item 75      Before "all" insert
    "Inventors"      -- Egon Roesch, Mannheim, --.

Signed and Sealed this

Twenty-second Day of January 1985

[SEAL]

*Attest:*

DONALD J. QUIGG

*Attesting Officer*      *Acting Commissioner of Patents and Trademarks*